(12) United States Patent
Doerr et al.

(10) Patent No.: US 8,554,300 B2
(45) Date of Patent: Oct. 8, 2013

(54) MRI GRADIENT FIELD DETECTOR

(75) Inventors: Thomas Doerr, Berlin (DE); Ingo Weiss, Berlin (DE)

(73) Assignee: Biotronik CRM Patent AG, Baar (CH)

(*) Notice: Subject to any disclaimer, the term of this patent is extended or adjusted under 35 U.S.C. 154(b) by 479 days.

(21) Appl. No.: 12/958,551

(22) Filed: Dec. 2, 2010

(65) Prior Publication Data

US 2011/0152667 A1 Jun. 23, 2011

Related U.S. Application Data

(60) Provisional application No. 61/288,855, filed on Dec. 22, 2009.

(51) Int. Cl.
*A61B 5/055* (2006.01)

(52) U.S. Cl.
USPC .......................................... 600/409

(58) Field of Classification Search
USPC .......................................... 600/409
See application file for complete search history.

(56) References Cited

U.S. PATENT DOCUMENTS

| | | | |
|---|---|---|---|
| 5,697,958 A * | 12/1997 | Paul et al. .................. | 607/31 |
| 2004/0088012 A1 | 5/2004 | Kroll et al. | |
| 2006/0293591 A1 | 12/2006 | Wahlstrand et al. | |
| 2008/0154342 A1 | 6/2008 | Digby et al. | |

FOREIGN PATENT DOCUMENTS

| | | |
|---|---|---|
| EP | 1716878 | 11/2006 |
| EP | 1935450 | 6/2008 |
| WO | WO 96/41203 | 12/1996 |

OTHER PUBLICATIONS

European Search Report Dated Apr. 8, 2011 (6 pages).

* cited by examiner

*Primary Examiner* — Christopher D Koharski
*Assistant Examiner* — Michael Carey
(74) *Attorney, Agent, or Firm* — ARC IP Law, PC; Jospeh J. Mayo

(57) ABSTRACT

A device and a method are disclosed for detecting electromagnetic fields, in particular, fields occurring in magnetic resonance tomography (MRT) or magnetic resonance imaging (MRI) tests. An implantable medical device (IMD), contained in a hermetically sealed housing, includes a control unit, a programming coil, and a communication unit, wherein the communication unit, together with the programming coil, is designed to allow communication between an external programming device and the IMD by utilizing alternating electromagnetic fields, and further comprising a detection unit for MRT interference fields, characterized in that the detection unit is designed in such a way that voltage profiles induced in the programming coil and originating from a pulsed alternating electromagnetic field of the MRT (gradient field) are detected, and a corresponding MRT detection signal is transmitted from the detection unit to the control unit, if communication with a programming device is not detected at the same time.

15 Claims, 4 Drawing Sheets

MRI GRADIENT FIELD DETECTOR

RELATED APPLICATION

This patent application claims the benefit of U.S. Provisional Patent Application No. 61/288,855, filed on Dec. 22, 2009, which is hereby incorporated by reference in its entirety.

TECHNICAL FIELD

The invention relates to a device and a method for detecting electromagnetic fields, in particular fields occurring in magnetic resonance tomography (referred to below as "MRT" or "MRI") imaging devices.

BACKGROUND

Although MRI testing is becoming increasingly important in diagnostic medicine, it is contraindicated for some patients. Such contraindication may result from an active implanted medical device (also referred to below as "implant" or "IMD"). Besides MRI testing, however, other technical applications pose a risk to the user of medical devices or implantable medical devices, particularly when such applications generate strong electromagnetic interference (EMI) fields in their surroundings.

In order to still allow MRI testing, various approaches are known which relate either to performing the MRI testing or to the implantable medical device.

Among others, technologies based on conventional processes for identifying magnetic fields are known for detecting magnetic fields. US 2008/0154342 A1 describes a method which uses a giant magnetoresistance (GMR) sensor to detect problematic magnetic fields from MRT devices.

An approach also exists in US 2006/0293591 A1, the object of which is to perform MRI detection based on evaluation of voltages at the communication coil and an electrode. However, this approach has the disadvantage that performing strictly voltage evaluation is very nonspecific for detecting a gradient field. The voltages induced at the programming coil 240 by the gradient field are extremely variable. The same applies for the voltages at the electrode, which are typically induced by the RF field and the gradient field. In addition, in this case additional voltage converters are necessary to allow simultaneous voltage measurement at the communication coil and at at least one electrode. Furthermore, there are configurations of the position of the magnetic field relative to the position of the implant which prevent detection of the gradient field.

The object of the present invention, therefore, is to provide a simple and reliable device and method for detecting typical MRT fields for an IMD which eliminate the disadvantages of the prior art.

SUMMARY

The object is achieved by use of the implantable medical device (IMD) and method claimed.

The IMD comprises at least the following: a hermetically sealed housing, at least one control unit, at least one programming coil 240, at least one communication unit, and a detection unit 250 for MRT interference fields, wherein the communication unit in cooperation with the programming coil 240 is designed to allow communication between an external programming device and the implanted medical device 200 by utilizing alternating electromagnetic fields, the detection unit 250 for MRT interference fields being designed in such a way that voltages or voltage profiles induced in the programming coil 240 and originating from a pulsed electromagnetic alternating field of the MRT are detected, and an MRT detection signal is transmitted from the detection unit 250 for MRT interference fields to the at least one control unit, provided that communication with an external programming device via the programming coil is not detected at the same time. The pulsed alternating electromagnetic fields may in particular be gradient fields. A particular advantage of the detection of pulsed alternating electromagnetic fields is that on the one hand the detection of interference fields typical for MRI is simplified, and on the other hand so-called "oversensing" is also avoided. In this context, "oversensing" is understood to mean that an IMD interprets a pulsed magnetic interference as a signal from the heart, and therefore it is no longer possible to draw correct conclusions concerning the health status of the patient. Such "oversensing" is avoided due to the explicit detection of pulsed electromagnetic interferences. In addition, the detection of the pulsed MRI gradient fields allows the MRI-related interferences to be differentiated from other electromagnetic interferences.

It is preferred that the detection unit 250 for MRT interference fields identifies the pulsed alternating electromagnetic fields by detecting a threshold value and counting the induced voltage pulses per unit time.

It is likewise preferred that the MRT interference detection is based on evaluation and comparison of the induced voltages or of the spectrum of the induced voltages with induced voltages typical for MRT or induced voltage spectra typical for MRT.

It is also preferred that the IMD is additionally connected to at least one electrode which is connected to the detection unit 250 for MRT interference fields, and an MRT detection signal is transmitted only when the interference is simultaneously detected via the programming coil 240 and via at least one electrode.

In a further preferred embodiment, the MRT detection signal causes a change in the operating state of the IMD, preferably to an MRT-safe state, this state being either permanent until a possible reprogramming, or temporary for a predetermined time period, or being maintained until there is no MRT detection or until there is no MRT detection for a predetermined time period.

It is also preferred that the detection of the gradient field is carried out using a programmable filter and a trigger unit which are connected to the programming coil 240, so that by programming of the filter the gradient field detection may be adapted to different MRT systems, and/or may be automatically adapted.

It is likewise preferred that an MRT state may be set permanently, until the next reprogramming, or for a predetermined or settable first time period, in which the VF detection is extended by a predetermined second time period in order to ensure gradient field detection, even for temporary zero crossings of the gradient fields in the plane of the implant. This ensures that detection of the gradient fields is possible or at least very probable, even for unfavorable positions of the implant with respect to the gradient fields, since the position of the gradient fields generally changes over time to allow imaging of various regions in an MRI test. In this regard VF (ventricular fibrillation) is understood not only as ventricular fibrillation, but also as any rapid or overly rapid disturbance in cardiac rhythm, wherein the concept of "overly rapid" may be different for each individual patient, depending on the condition of the circulatory system. All ventricular tachycardia is explicitly encompassed by the term "VF."

In a further preferred embodiment, the extension of the VF detection by the second time period is up to 30 s, preferably up to 10 s.

It is also preferred that the detection unit 250 for MRT interference fields may be connected to at least one further MRT sensor and/or indicator for MRT interference fields, and the MRT detection is based on detection by at least one of the sensors and/or indicators. In the context of the present patent application, the terms "MRT sensor" and "MRT indicator" are each understood to mean all sensors, devices, or components which allow detection of MRT fields or other strong electromagnetic fields. These include, but are not limited to, GMR sensors, MagFET sensors, Hall sensors, monitoring of battery voltages during capacitor charging processes, detection of RF fields, detection of currents induced by electromagnetic fields, detection by light-emitting diodes which are excited to emit light by MRT fields, and detection of specific vibrations, or components designed as sensors for detection of vibrations induced by Lorentz forces. In addition, a position sensor, in particular a self-calibrating position sensor, may be used to increase the specificity of the MRT detection.

It is further preferred that a position sensor is used for plausibility checking, and a positive MRI identification is made only when the position sensor reports a prone posture and/or another presettable posture.

The position sensor is particularly preferably self-calibrating, the calibration taking place under presettable boundary conditions such as, but not limited to, times of day and/or heart rates and/or respiratory rate and/or hemodynamic parameters and/or activity (motion sensor).

It is also preferred that at least one of the following measures is introduced for MRT detection or by the MRT detection signal:

Changing to an MRI-safe state,

Remaining for a prolonged period of time in an MRI-safe state or a state that is insensitive to electromagnetic interference fields, Synchronization of electrical measurements (impedance measurements, for example) using field intensity minimum values occurring with periodic or pulsed electromagnetic fields, or synchronization of a stimulation using these same minimum values, and Emission of electromagnetic pulses for signaling that a medical device, in particular an implant, is present in the electromagnetic field, in particular for signaling to an MRI device, with the possibility of thus transmitting information as well as the interference and displaying same on the MRI screen.

The object is further achieved by the method according to Claim 11. The method for detecting pulsed magnetic alternating fields using an IMD provides that the IMD detects voltages induced in the programming coil by pulsed alternating electromagnetic fields, and as a function of the detected induced voltage profiles generates a signal in the IMD and relays the signal to a control unit in the IMD, provided that communication with a programming device via the programming coil is not detected at the same time. The method may be carried out in particular using an IMD of Claims 1 through 10.

DETAILED DESCRIPTION

Figure 1:
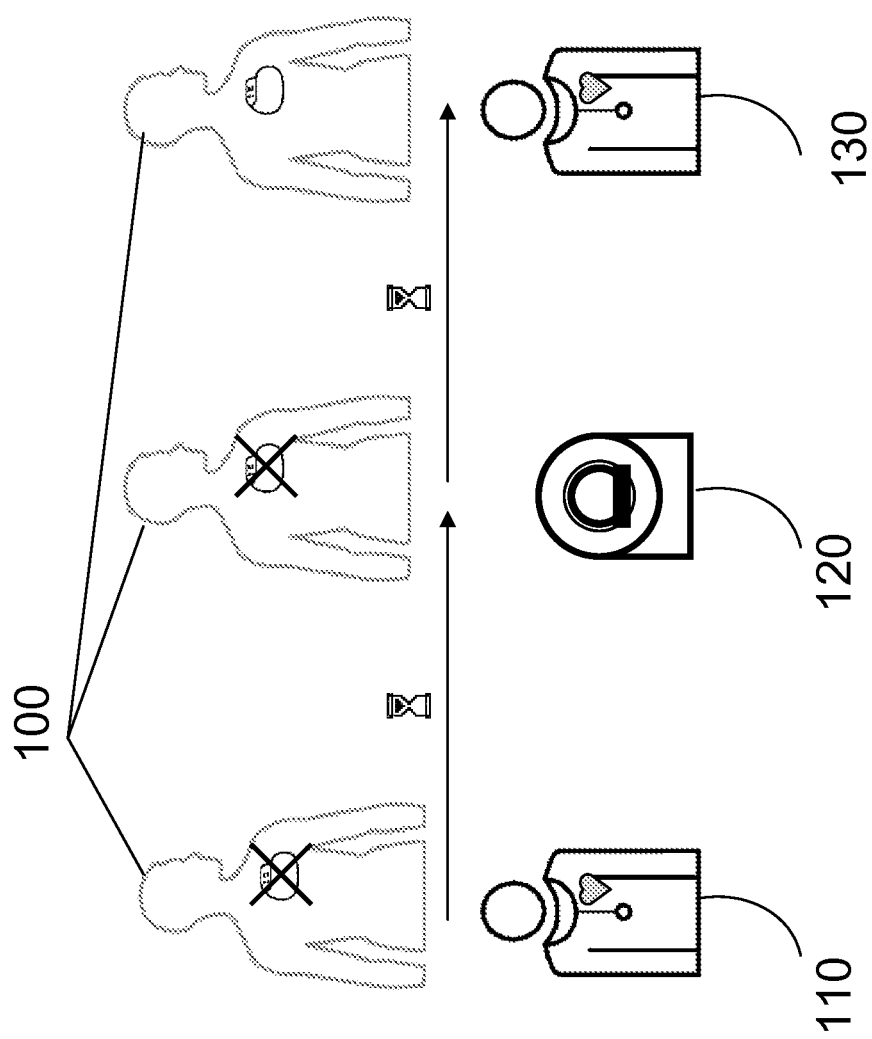
FIG. 1 shows a schematic illustration of the sequence of a prior art MRT test.

FIG. 1 illustrates the starting situation, i.e., the current clinical prior art. An ICD patient 100 receives follow-up care from a first cardiologist 110 before the planned MRT test, at which time the ICD is switched off. After a first time delay of hours to days the MRT test is performed by a radiologist 120. After a further time delay the patient is once again under the care of a second cardiologist 130 (who may or may not be the same as first cardiologist 110), at which time the ICD is switched back on. During the two time delay intervals, the patient 100 is without the protection of the implanted defibrillator, and is essentially without rhythm monitoring. This residual risk is currently accepted in return for the benefits of the MRT test. In addition, the economic and logistic expenditure for such a procedure is very high, and in many cases rules out emergency use of MRT. The procedure is similar to that for pacemaker patients and patients having other implants, wherein the devices do not necessarily have to be placed in an inhibited mode; instead, other operating modes may be used, depending on the individual patient. However, all the processes have the common feature that before, during, and after the MRT test the patient is not provided with optimal care.

Figure 2:
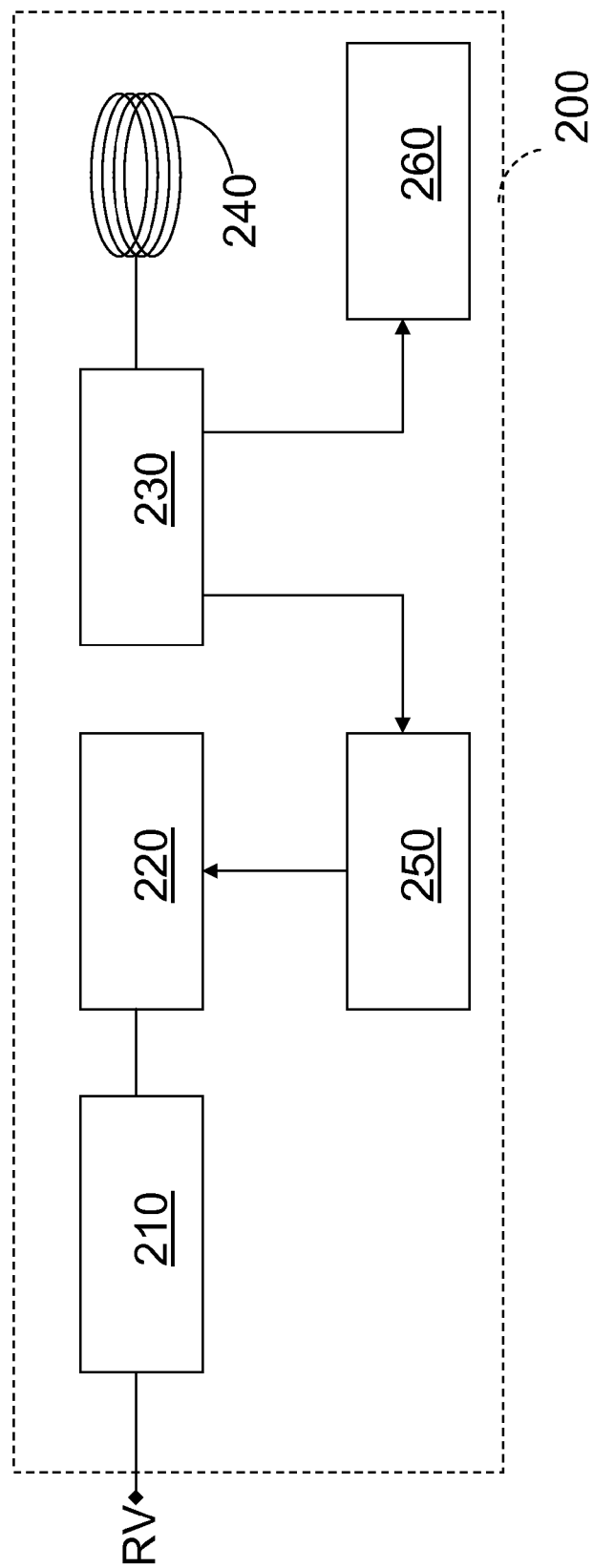
FIG. 2 shows a block diagram of an IMD according to the invention, having a detection unit for MRT interference fields.

FIG. 2 illustrates a novel approach for detecting an MRT interference field in the electronic implant 200. For simplicity of the illustration a single-chamber pacemaker has been selected as an example; however, it is noted that dedicated monitoring devices or multichamber devices, such as two-, three-, or four-chamber systems or other neurostimulators, may be used. A right ventricular (RV) pacemaker electrode is connected to a sensing stage 210. The sensing stage 210 is connected to the pacemaker timer 220. This timer 220 usually operates in a demand-controlled mode (for example, VVI mode).

A programming coil 240 enclosed by the metallic housing of the implant is usually present for communication between the electronic implant and an external programming device. The communication takes place by means of near field telemetry that involves magnetic alternating fields. For this purpose the programming coil 240 is connected to a transceiver 230, which in turn is connected to a read/write unit 260 for reading from and writing to the memory in the implant 200. Thus, it is possible to read data from the implant and also to write parameters to the memory of the implant.

According to the invention, the transceiver is also connected to a detection unit 250 for MRT interference fields. This unit evaluates the typical interference patterns of an MRT gradient field, coupled to the programming coil 240. The detection unit 250 for MRT interference fields is in turn connected to the pacemaker timer 220. If an MRT gradient field is sensed in the surroundings of the electronic implant 200, the detection unit 250 for MRT interference fields automatically switches the pacemaker timer 220 to an operating mode defined as MRT-safe (for example, V00 mode for patients dependent on a pacemaker).

As mentioned above, alternative examples may be implemented in an implanted cardioverter-defibrillator (ICD), neurostimulator, cardiac resynchronization therapy (CRT) device, monitoring implant, or an implantable medication pump.

Figure 3:
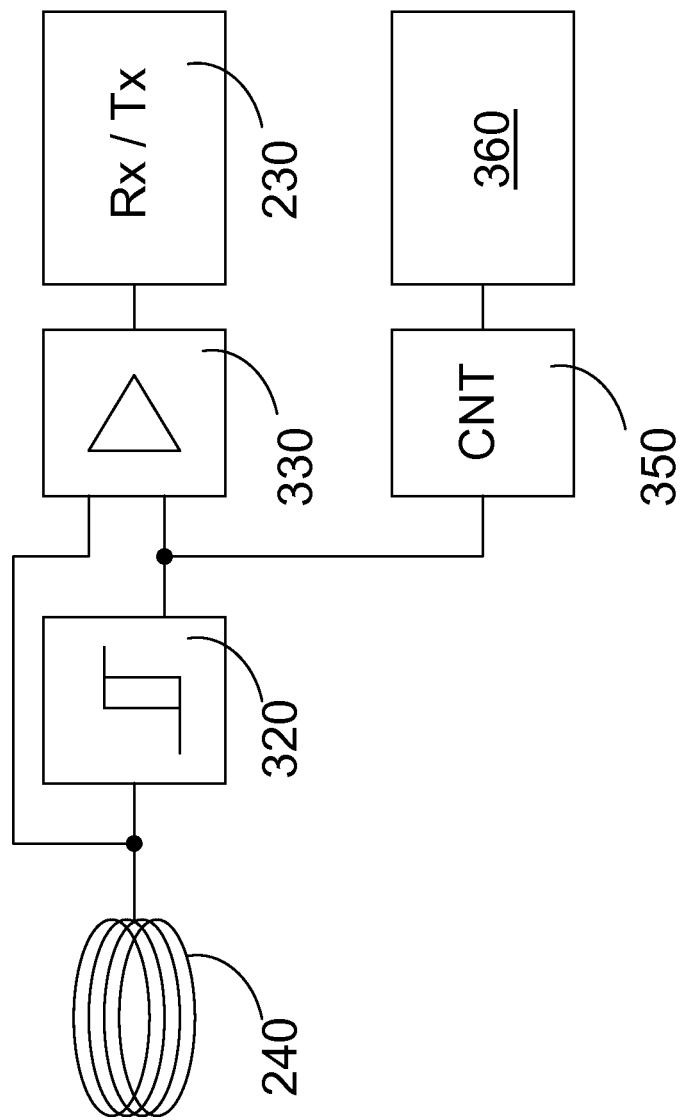
FIG. 3 shows a block diagram of an IMD according to the invention, having a simple gradient field detector.

FIG. 3 shows a simple implementation of the detection unit 250 for MRT interference fields that may also serve as a gradient detection unit, which could be retrofitted to existing pacemaker or ICD systems. Signals from the programming coil 240 are usually sent to the transceiver 230 as amplified signals. However, this so-called programming amplifier 330 consumes considerable power, so that it is usually switched off, and is activated only when an additional, nonspecific trigger unit 320 senses a signal level at the programming coil 240. This trigger unit 320 then activates the programming amplifier 330, thus starting the evaluation of the programming signals in the transceiver 230.

According to the invention, the output signal of the trigger unit 320 is also sent to a counter unit 350. This counter unit 350 is configured in such a way that it generates an output signal whenever the input signal frequency could correspond to a typical MRT gradient field, and thus signals that an MRT gradient field is suspected. To differentiate this "suspicion" from a true programmer communication, the counter unit 350 is connected to an additional evaluation unit 360, which initiates switching to an MRT-safe mode only when a programmer communication is not running at the same time. For the differentiation, this evaluation unit may also make use of additional criteria, for example simultaneous onset of interferences (noise) at an electrode interface, caused by RF fields typically associated with MRT.

Figure 4:
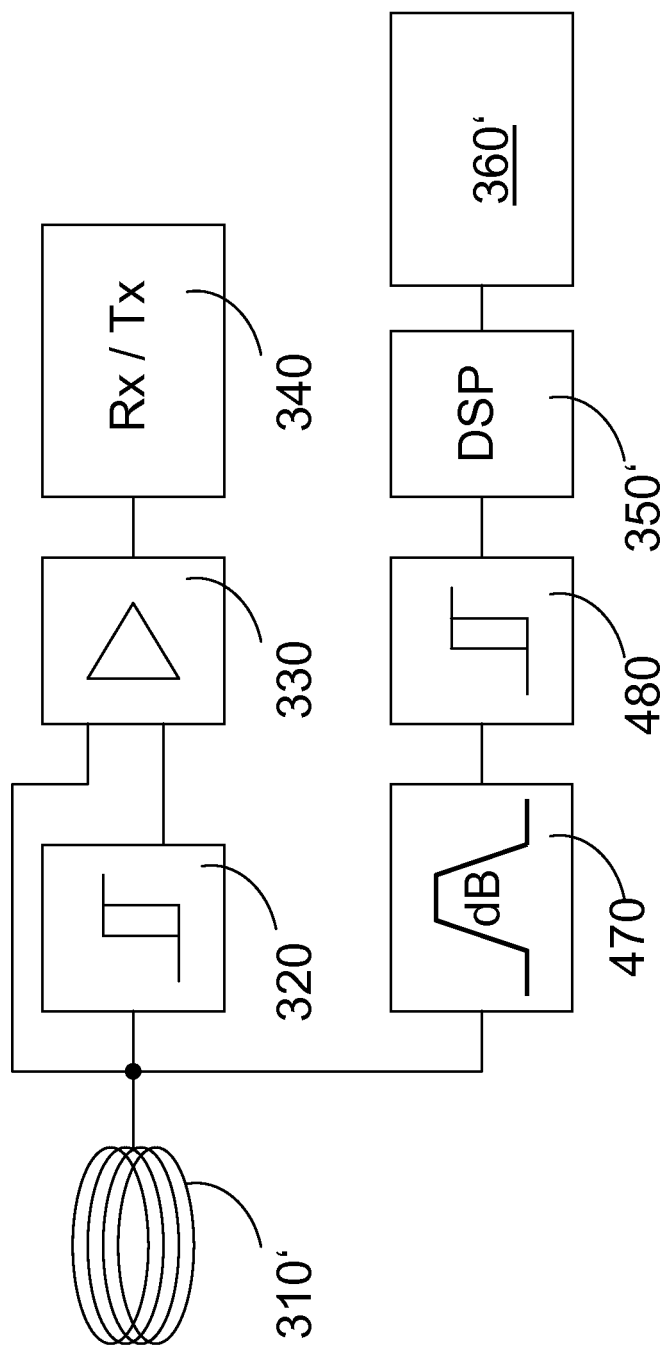
FIG. 4 shows a block diagram of an IMD according to the invention, having a specifically programmable gradient field detector.

FIG. 4 shows an expansion of the detection unit illustrated in FIG. 3 for MRT interference fields, in particular, for gradient fields. In the present case a signal from a programming coil 310' for gradient field detection is first filtered from the typically expected MRT gradient field by means of a programmable filter 470, so that a subsequent separate, programmable trigger unit 480 delivers a signal only when interference occurs in the frequency spectrum of an MRT gradient field that appears at the programming coil 310'. In addition, instead of the above-referenced counter unit 350, an algorithmic evaluation of the gradient signals may be carried out, for example in a digital signal processor 350', to be able to reliably differentiate the typical repetition rates and patterns of an MRT gradient field from other interference signals. This has the advantage that the detection unit 250 for MRT interference fields or the gradient field detector may be specifically adapted to a defined MRT system, and the risk of inadvertent switching to an MRT-safe state is minimized, which increases the specificity of the detection unit 250 for MRT interference fields. The DSP is connected to an additional evaluation unit 360' as shown.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device (IMD) contained in a hermetically sealed housing, comprising:
   a programming coil enclosed by said hermetically sealed housing;
   a communication unit coupled with the programming coil, wherein the communication unit is configured to enable communication between an external programming device and the IMD by utilizing alternating electromagnetic fields;
   a detection unit configured to sense MRT interference fields, wherein voltage pulses induced in the programming coil and originating from a pulsed alternating electromagnetic field of the MRT are detected; and
   a control unit that configured to receive an MRT detection signal from the detection unit, wherein communication with the external programming device via the programming coil is not detected at the same time;
   wherein the IMD is connected to at least one electrode which is connected to the detection unit, and
   wherein the MRT detection signal is transmitted only when the sensed MRT interference fields is simultaneously detected via the programming coil enclosed by said hermetically sealed housing and via the at least one electrode.

2. The IMD according to claim 1, wherein the detection unit identifies the pulsed alternating electromagnetic fields by detecting a threshold value and counting the induced voltage pulses per unit time.

3. The IMD according to claim 1, wherein the MRT interference detection is based on evaluation and comparison of characteristics of the induced voltage pulses with voltage pulse characteristics typically associated with MRT.

4. The IMD according to claim 3, wherein said voltage pulse characteristics include frequencies.

5. The IMD according to claim 1, wherein the MRT detection signal is configured to cause a change in an operating state of the IMD.

6. The IMD according to claim 1, wherein the detection of the pulsed alternating electromagnetic fields is accomplished using a programmable filter and a trigger unit connected to the programming coil.

7. The IMD according to claim 1, wherein an MRT state may be set either permanently, until a next reprogramming, or for a predetermined or settable first time period, and VF detection is extended by a predetermined second time period in order to ensure detection of the pulsed alternating electromagnetic fields, even for temporary zero crossings of gradient fields in the plane of the implant.

8. The IMD according to claim 7, wherein the extension of the VF detection by the second time period is up to 30 s, preferably up to 10 s.

9. The IMD according to claim 1, wherein the detection unit is connected to an indicator of MRT interference fields and an MRT sensor configured to sense MRT interference fields, wherein the MRT detection occurs in response to detection by the sensor.

10. The IMD according to claim 1, wherein at least one of the following measures is introduced in response to MRT detection:
    changing to an MRI-safe state;
    remaining for a prolonged period of time in an MRI-safe state that is insensitive to electromagnetic interference fields;
    synchronization of electrical measurements using field intensity minimum values occurring with periodic or pulsed electromagnetic fields;
    synchronization of a stimulation using the field intensity minimum values; and
    emission of electromagnetic pulses configured to signal that the IMD is present in the electromagnetic field, in particular to signal to an MRI device, with the possibility of transmitting information as well as the interference, and displaying the information and the interference on an MRI screen.

11. A method for detecting pulsed magnetic alternating fields using an IMD contained in a hermetically sealed housing and equipped with a control unit and a programming coil enclosed by said hermetically sealed housing, comprising:
    detecting voltages induced in the programming coil by pulsed alternating electromagnetic fields;

sensing interference fields, generating a signal in the IMD as a function of the detected induced voltages;

relaying the signal to the control unit, wherein communication with a programming device via the programming coil is not detected at the same time;

wherein the IMD is connected to at least one electrode, and wherein the relayed signal is transmitted only when the interference fields is simultaneously detected via the programming coil enclosed by said hermetically sealed housing and via the at least one electrode.

12. The IMD according to claim 1, further comprising a transceiver coupled to the programming coil, a programming amplifier and a trigger unit configured to sense a signal level at the programming coil.

13. The IMD according to claim 12, wherein the programming amplifier is configured to remain switched off and is only activated when the trigger unit senses the signal level at the programming coil, such that when the trigger unit senses the signal level at the programming coil, the trigger unit is configured to activate the programming amplifier.

14. The method according to claim 11, wherein the IMD further comprises a transceiver coupled to the programming coil, a programming amplifier and a trigger unit configured to sense a signal level at the programming coil.

15. The method according to claim 14, wherein the programming amplifier is switched off and is only activated when the trigger unit senses the signal level at the programming coil, such that when the trigger unit senses the signal level at the programming coil, the trigger unit activates the programming amplifier.

* * * * *